(12) United States Patent
Fretes

(10) Patent No.: US 12,181,460 B2
(45) Date of Patent: Dec. 31, 2024

(54) SEMICONDUCTOR NANOSENSING DEVICE WITH MULTILAYER GRAPHENE SHEET FOR SEQUENCING OR SENSING NUCLEIC ACIDS

(71) Applicant: Gentroma Inc., Flushing, NY (US)

(72) Inventor: Krista Fretes, Flushing, NY (US)

(73) Assignee: Gentroma, Inc., New York, NY (US)

( * ) Notice: Subject to any disclaimer, the term of this patent is extended or adjusted under 35 U.S.C. 154(b) by 0 days.

(21) Appl. No.: 18/039,209

(22) PCT Filed: Nov. 29, 2021

(86) PCT No.: PCT/US2021/072616
§ 371 (c)(1),
(2) Date: May 26, 2023

(87) PCT Pub. No.: WO2022/115873
PCT Pub. Date: Jun. 2, 2022

(65) Prior Publication Data
US 2024/0003866 A1    Jan. 4, 2024

Related U.S. Application Data

(60) Provisional application No. 63/222,803, filed on Jul. 16, 2021, provisional application No. 63/119,040, filed on Nov. 30, 2020.

(51) Int. Cl.
*G01N 27/327* (2006.01)
*B82Y 5/00* (2011.01)
(Continued)

(52) U.S. Cl.
CPC .......... *G01N 33/48721* (2013.01); *B82Y 5/00* (2013.01); *B82Y 30/00* (2013.01); *G01N 27/3278* (2013.01); *G01N 27/44791* (2013.01)

(58) Field of Classification Search
CPC ..... G01N 33/48721; B82Y 5/00; B82Y 30/00
See application file for complete search history.

(56) References Cited

U.S. PATENT DOCUMENTS

| 8,936,763 B2 | 1/2015 | Rothberg et al. |
|---|---|---|
| 9,921,157 B2 | 3/2018 | Rothberg et al. |
| | (Continued) | |

FOREIGN PATENT DOCUMENTS

WO    2020223271 A1    11/2020

OTHER PUBLICATIONS

Wu et al., "Fabrication of nanopore in graphene by electron and ion beam irradiation: Influence of graphene thickness and substrate ," Computational Materials Science 102 (2015) 258-266 (Year: 2015).*

(Continued)

*Primary Examiner* — Alexander S Noguerola
(74) *Attorney, Agent, or Firm* — Andrew H. Berks

(57) ABSTRACT

A nanosensing device is disclosed for high throughput nucleic acid sequencing or sensing. The device is a silicon chip, having a silicon nitride top layer, an opening through the chip, a hole in the top layer, and a graphene sheet over the top layer and hole. A graphene layer with a p-type crinkle ruga is placed over the hole, and one of more nanopores in the graphene layer may be provided over the hole. A nucleic acid strand transported to the chip may be translocated through a nanopore and the hole by microfluidic forces. An electrical potential across the nanopores can be measured with a patch clamp amplifier to make nucleobase assignments and sequence the DNA. Alternatively, there are no nanopores and the interaction with the crinkle ruga is used to sense the presence of a nucleic acid polymer.

15 Claims, 5 Drawing Sheets

(51) Int. Cl.
  *B82Y 30/00* (2011.01)
  *G01N 33/487* (2006.01)
  *G01N 27/447* (2006.01)

(56) References Cited

U.S. PATENT DOCUMENTS

2015/0069329 A1* 3/2015 Jeon .................... B81C 1/00087
  257/29
2023/0159870 A1* 5/2023 Washio .................... C12M 1/34
  702/19

OTHER PUBLICATIONS

Kirilenko et al., "Measuring the corrugation amplitude of suspended and supported graphene," Physical Review B 84, 235417 (2011) (Year: 011).*

Traversi, et al., "Detecting the translocation of DNA through a nanopore using graphene nanoribbons", Nature Nanotechnology, Dec. 2013, vol. 8, pp. 939-945, Macmillan Publishers Limited.

Heerema et al., "Graphene nanodevices for DNA sequencing", Nature Nanotechnology 2016, vol. 11, pp. 127-136.

Hwang, et al., "Ultrasensitive detection of nucleic acids using deformed graphene channel field effect biosensors", Nature Communications 2020, 11, Article No. 1543.

Verschueren, et al., "Label-Free Optical Detection of DNA Translocations through Plasmonic Nanopores". ACS Nano 2019, 13, 61-70, DOI: 10.1021/acsnano.8b06758.

Feng, et al., "Nanopore-based Fourth-generation DNA Sequencing Technology. Genomics, Proteomics & Bioinformatics", 2015, vol. 13, pp. 4-16.

Li, R.; Kothari, M.; Landauer, A. K.; Cha, M.-H.; Kwon, H.; Kim, K.-S., A New Subcritical Nanostructure of Graphene-Crinkle-Ruga Structure and Its Novel Properties. MRS Advances 2018, 3, 2763-2769, DOI: 10.1557/adv.2018.432.

Paulechka et al., "Nucleobase-functionalized graphene nanoribbons for accurate high-speed DNA sequencing", Nanoscale 2016, 8, 1861-1867, DOI: 10.1039/C5NR07061A.

Derrington et al., "Nanopore DNA sequencing with MspA", Proceedings of the National Academy of Sciences 2010, 107, 16060-16065, DOI: 10.1073/pnas.1001831107.

Manrao et al., "Nucleotide Discrimination with DNA Immobilized in the MspA Nanopore", PLOS ONE 2011, 6, e25723, DOI: 10.1371/journal.pone.0025723.

Venkatesan et al. "Highly Sensitive, Mechanically Stable Nanopore Sensors for DNA Analysis", Advanced Materials 2009, 21, 2771-2776.

Liu et al., "Fast and controllable fabrication of suspended graphene nanopore devices", Nanotechnology 2012, 23, 085301, DOI: 10.1088/0957-4484/23/8/085301.

"KOH Etching of Bulk Silicon". NanoFAB, University of Alberta, Ed.2013.

Stranges et al., Design and characterization of a nanopore-coupled polymerase for single-molecule DNA sequencing by synthesis on an electrode array. Proceedings of the National Academy of Sciences 2016, vol. 113, pp. E6749-E6756, DOI: 10.1073/pnas.1608271113.

Rang et al., "From squiggle to basepair: computational approaches for improving nanopore sequencing read accuracy", Genome Biology 2018, vol. 19, p. 90, DOI: 10.1186/s13059-018-1462-9.

NXTGNT 2020 https://www.nxtqnt.ugent.be/10x~genomics-single-cell-and-linked-read-sequencing/ (Accessed: Nov. 4, 2020).

Deamer et al., "Characterization of Nucleic Acids by Nanopore Analysis", Accounts of Chemical Research 2002, 35, 817-825, DOI: 10.1021/ar000138m.

Wang et al., "The evolution of nanopore sequencing", Frontiers in Genetics 2015, 5, DOI: 10.3389/fgene.2014.00449.

International Search Report and Written Opinion for PCT International Patent Application PCT/US21/72616, mailing date of Feb. 25, 2020.

* cited by examiner

SEMICONDUCTOR NANOSENSING DEVICE WITH MULTILAYER GRAPHENE SHEET FOR SEQUENCING OR SENSING NUCLEIC ACIDS

FIELD OF THE INVENTION

This invention pertains to nucleic acid sequencing and sensing using a chip employing a multilayer graphene nanostructure and a p-type crinkle ruga over at least one hole in the chip.

BACKGROUND

Generations of DNA sequencing technologies, from Sanger sequencing to nanopore sequencing, have been developed to address the important applications of genetic sequencing, of which the most essential is personalized medicine for a e.g., cancer, genetic disorders, and complex disease treatments. Additional applications that also require efficient DNA sequencing platforms include vaccine research, epidemic prevention, food monitoring, forensic sample analysis, genetic drug development, and consumer genetic testing, among various others. While most current sequencing methods involve chemically altering, amplifying, and labeling the DNA, certain applications in personalized medicine and single cell sequencing require label-free and real-time sequencing that can retain the original DNA sample and accomplish faster turnaround times within the span of a few hours.

Nanopore sequencing is one current technology[1-3], and the only currently well-known method that is label-free and well-studied in the field of DNA sequencing. A DNA or RNA sample is passed through an electric field in solution and is directed into either a biological or solid-state nanopore embedded in a membrane substrate [4]. Real-time changes in the ionic current running through the membrane are caused when DNA bases translocate through the nanopore as a result of the electric field and are measured by a sensitive current-measuring detector. Nanopore sequencing has allowed real-time sequencing without the need to label DNA and has now even advanced to 1-2 Mb read lengths in one run [5].

While this method exhibits capability for reasonably long-read DNA sequencing, problems are present that deter its efficiency and ability to make personalized medicine, as well as other awaited applications an established reality. First, while commercially available devices can provide speeds up to 250 bases/s, the speed is not suitable for personalized medicine applications, where a multitude of genomes must be sequenced much more rapidly. Secondly, a sub-99% base accuracy is reasonable for many applications but is not sufficient for haplotyping and personalized medicine. Thus, much progress still needs to be made in this technology for some of the most essential genomic sequencing applications to become commonplace.

This invention presents an alternate setup and method to detect measurable changes in ionic current due to base translocation via a nanopore within a novel nanostructure made of graphene that can make sequencing much faster, more accurate, as well as high-throughput. Graphene is attractive as a nanopore substrate material due to graphene's ability to form atomically thin pores and different structures [6]. Main configurations of graphene nanostructures used in the field of sequencing include graphene nanopores, sheets, nanotubes, and nanogaps. Recently, a new shape has been described in a study by Kim et al regarding a "crinkle ruga" structure, which is when graphene buckles over rectangular grooves to form a valley [7]. The crinkles have sawtooth-shaped profiles with their faces perfectly flat and the tips of the peaks and valleys highly curved. Crinkle ruga structures have a flexoelectric effect, or an electromechanical coupling of polarization and strain gradient. As demonstrated with a silica or silicon substrate, graphene buckles inward when strain is applied, which creates a gradient of negative or positive charges, respectively, accumulating at the crinkle valley, a polarization density effect of the flexoelectric effect. The type of charge accumulated depends on the material with the grooves, as Van Der Waals forces present at the edges of the grooves in the material will directly contribute to the flexoelectric coupling effect of the graphene with the material. Control of the structure properties and localization with the substrate choice and radius of curvature used to buckle the graphene is additionally described. Kim et al further studied molecular effects, such as observations of linearizing strands of DNA, at the crinkle, which points to the possibility of using graphene crinkles to study and control location of polar molecules. This is one of the many benefits of graphene in the study of many biomolecules in the field.

For DNA sequencing, graphene has been shown to be capable of ultrafast sequencing, evident in a NIST study where translocation may permit speeds of up to 66 million bases per second [8]. Due to these speeds, methods to control DNA translocation are required for electrical detection, requiring a specific electrolyte solution which can add to complications while successfully slowing down DNA translocation, such as adding more noise to signal measurement. Additionally, another feature that hinders the effectiveness of current nanopore sequencing is that the orientation of nucleobases within the pore impacts the ionic current signal, thus being one reason for the <99% accuracy rate of this method. Nanopore sequencing probes the structural property of nucleobases and depends on the structural characteristics to create an electronic fingerprint in the current signal, which leads to signal overlapping between structurally similar guanines and adenines, as evidenced in Derrington et al, [9] and Manrao et al. [10]. Nanopore sequencing can be improved if it can incorporate an alternative method of physical measurement in addition to the electronic measurements, as well as a way to distinguish each base using other features, such as molecular interactions, in addition to just sampling base dimensions.

By applying an external voltage, molecules with sizes slightly smaller than the pore size are passed through the pore from an electrostatic potential. The nanometer-sized pores are usually embedded in a biological membrane, normally protein nanopores, which exhibit numerous problems with the control of translocation as well as accuracy [5]. They are also formed in solid-state films, such as silicon or graphene, which separates two reservoirs containing conductive electrolytes into cis and trans compartments. Electrodes immersed within each chamber generate fields and help detect electronic signals. Under a biased voltage, electrolyte ions in solution are moved through the pore electrophoretically, thereby generating an ionic current signal. When the pore is blocked by an analyte, such as a negatively charged DNA molecule added to a cis chamber, current flowing through the nanopore would be blocked, interrupting the current signal [5]. The physical and chemical properties of the target molecules can be calculated by statistically analyzing the amplitude and duration of transient current blockades from translocation events (Venkatesan et al, [11]). Solid-state nanopores have many advantages over biological nanopores, including more stability. Graphene nanopores, in particular, exhibit an extraordinarily high potential for DNA sequencing, showing increased spatial resolution.

The fast translocation of DNA bases presents an issue with current sequencing using nanopores [12]. Nucleotides provide unique electronic signatures with regards to orientation in the pore and charge properties [5]. Controlling the position of the nucleotides within the nanopore will be instrumental to improving nanopore sequencing accuracy and utility.

This invention addresses the ongoing need for fast, inexpensive, and high-throughput nanopore devices for molecular detection that can be used in the field to sequence real-time and label-free nucleic acid samples. Quick and inexpensive yet accurate DNA sequencing is an ongoing challenge. The field of personalized medicine can be greatly benefitted with a device that allows for real-time sequencing compatible with droplet-based methods of transferring DNA, which can lead to rapid sequencing of many genomes in a shorter span of time, which is especially required for fields regarding newborn health analysis and pandemic crises. Nanopores of current devices still require specific electrolyte solutions and environments of the DNA, which hinders progress in this area and slows transition of nanopore sequencing into some fields.

In view of these existing technologies, there is a current need for technology that improves on nanopores by providing for the direct and diverse measurements of shifts in electronic signals in order to match the translocation speeds of nucleobases in the pore. Necessary as well are nanopores that have higher capabilities of sensing by probing the molecular characteristics in conjunction with the interactive behavior of each nucleobase for better discrimination, and directly controlling molecular orientation within the nanopore for reproducible results with varied quality of the medium used. Such methods can flexibly work with a variety of solutions and methods for different needs and purposes across industry and research pursuits.

SUMMARY OF THE INVENTION

Accordingly, a chip is provided herein for sensing or sequencing a strand of nucleic acids. The chip may have a substrate fabricated from silicon about 1.0 mm to about 10 mm wide, about 1.0 mm to about 10 mm long, with a thickness of about 50 µm to 500 µm (preferably 200 µm), wherein the substrate has a top layer of silicon nitride ($Si_3N_4$) with a thickness of 20 nm to 500 nm (preferably about 200 nm), and optionally a bottom layer of silicon nitride with a thickness of 20 nm to 500 nm (preferably about 200 nm).

In an embodiment, the chip may have an opening in the bottom side leading to a window in the center of the chip 5-50 µm square (preferably 20 µm) penetrating from the optional bottom layer into the substrate of the chip, wherein the opening does not penetrate the top layer of silicon nitride. In an embodiment, a hole is provided in the in top layer of silicon nitride centered over the window, wherein the hole is 50 nm to 1000 nm (350-400 nm) wide and 50 nm to 1000 nm long, (500-600 nm) wherein the hole is in the shape of a circle or simple polygon (preferably an hourglass).

In an alternative embodiment, a hole is drilled through the chip with TEM or an electron beam, in which case there is no window but rather a straight shaft through the chip.

In an embodiment, a multilayer graphene about 1-60 nm thick is affixed to the SiN layer on the top substrate in a latitudinal orientation, and wherein the graphene sheet is subjected to lateral compression to cause a p-type crinkle ruga having a crease to form thereon over the hole, and the graphene sheet may have one or more nanopores 0.3 to 3.0 nm in diameter centered over the hole.

In an embodiment, the chip may have a pair of electrodes on opposite ends of the hole, where the electrodes are connected to a patch clamp amplifier capable of measuring an electric charge across the graphene sheet.

In an embodiment, a method of detecting nucleobases in a strand of nucleic acids is provided, comprising a chip with a graphene sheet and directing a saline solution of the nucleic acid comprising a strand of nucleobases toward a nanopore in the graphene sheet, wherein the nucleobase strand translocates through the pore and interacts with the layers of the multilayer graphene sheet, and the patch clamp amplifier measures changes in the ionic current and detects each nucleobase in the nucleic acid strand translocating through the nanopore and the nucleic acid sequence is assigned.

DETAILED DESCRIPTION

Figure 1A:
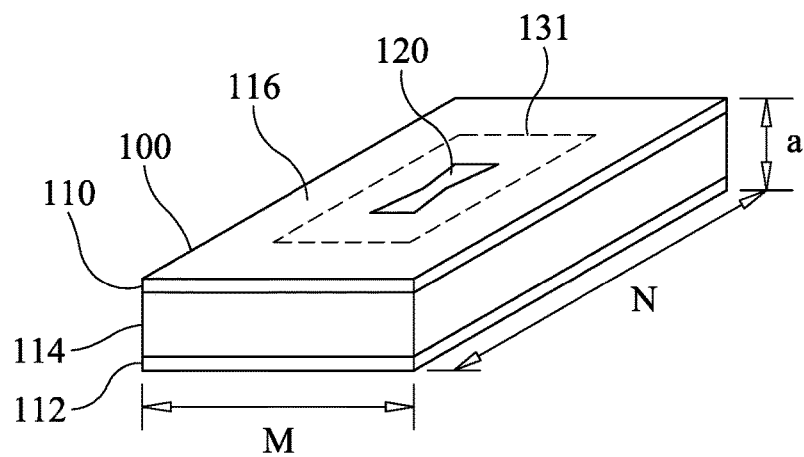
FIG. 1A is a perspective view of the top of a silicon/silica nitride chip according to an embodiment.

Disclosed herein is a nano-sensing device capable of very high throughput nucleic acid sequencing, in which a polarized graphene sheet or sheet interacts with a nucleic acid strand or polymer to detect and identify nucleobases in the nucleic acid strand. Alternatively, the device can sense a nucleic acid polymer. The device comprises a semiconductor chip having one or more holes drilled or etched thereon, and multilayer graphene (MLG) sheet layered over the top surface of the chip, wherein the graphene is subject to compression pressures to form a p-type crinkle ruga over each hole. Electromechanical effects of the fold of the crinkle ruga can draw nucleic acid polymers into the fold.

The nano-sensing device semiconductor chip has a "top side" and a "bottom side." The top orientation refers to (1) the side that the MLG is affixed to, and (2) the side that a nucleic acid polymer approaches the chip for sequencing or sensing. A nucleic acid polymer will interact with the graphene on the top surface of the chip in this invention for the sensing and sequencing embodiments of this invention.

In an embodiment, at least one nanopore is provided in the graphene sheet over a hole that forces a nucleic acid strand to translocate through the nanopore and align proximal to a sensor that can detect and identify nucleobases in a nucleic acid strand. Alternatively, no nanopore is employed.

Detection or sensing of the nucleobases that comprise the nucleic strand as they interact or translocate through the graphene can be accomplished by several methods. In an embodiment, ionic currents can be used with an ionic current detector that can determine electrical signatures of specific nucleobases as they translocate through a nanopore in a graphene sheet, and assign the nucleobases (A, C, T/U, G) based on the electrical characteristics. The ionic currents can be measured across a pair of electrodes on either side a hole in the chip.

The nucleic acid strand may comprise nucleotides or nucleosides, and may be from a natural source, such as isolated from a cell, such as a bacteria, plant or animal cell, or extracted from a viral source. A nucleic acid polymer may comprise deoxynucleic acid (DNA) or ribonucleic acid (RNA). As used herein, "nucleic acid strand" is equivalent to "nucleic acid polymer." The term "sensing" means detecting the presence of a nucleic acid, either generally or having a specific sequence, without elucidating the sequence of the nucleic acid.

In an embodiment, a device having nanopores is used to elucidate nucleic acid sequences, wherein a nucleic acid polymer translocates through the nanopore. In an embodiment, a device without nanopores used to sense a nucleic acid according to measured electrical characteristics across a pair of electrodes on either side of a hole, wherein a crinkle ruga over the hole interacts with the nucleic acid and provides a characteristic signature of an electric current across the hole caused by the interaction with a nucleic acid strand.

In an embodiment, this invention discloses a high-throughput single cell sequencing device capable of label-free sequencing that does not require chemical modifications or cell cultures of individual cells to be analyzed. The disclosed sequencing instrument may be capable of massive parallel and label-free sequencing that can be completed faster (under 2 hours) and cheaper than conventional technologies for single cell nucleic acid sequencing applications in the pharmaceutical industry, biotech R&D, and healthcare. In an embodiment, a platform is disclosed utilizing a nanopore sequencing technology, using graphene nanopores with optical or electrical properties that can detect and distinguish nucleic acid bases in a nucleic acid strand. The inventors have demonstrated interactions with DNA as proof-of-concept data for label-free and cost-effective sequencing. This invention may be able to integrate droplet transport of DNA fragments into our sequencer to directly read nucleotides via electrical or optical interactions in order to make single cell sequencing faster, high-throughput, and cost-effective for personalized medicine and applications in genetics and immunotherapy advancement.

As used herein, the term "about" implies a dimension that is not critically precise, and the term "about" implies ±20% of the stated value.

As shown in the Figures, the present application discloses an embodiment of a high-throughput nanopore bio-sensing device, comprising a chip 100 having a silicon substrate 114 about 1.0 mm to about 10 mm wide (FIG. 1A, dimension M), about 1.0 mm to about 10 mm long (FIG. 1A, dimension N). In an embodiment, the chip 100 is about 1.5 mm to about 3.0 mm wide and 1.5 mm to 3.0 mm long, or about 1.5 mm or 2.0 mm wide and about 1.5 mm or 2.0 mm long. In an embodiment, the overall thickness of chip 100 may be about 50 µm to 500 µm (FIG. 1A, dimension Q). In an embodiment, the overall thickness of chip 100 may be about 150 µm to 300 µm, or about 200 µm.

Figure 7:
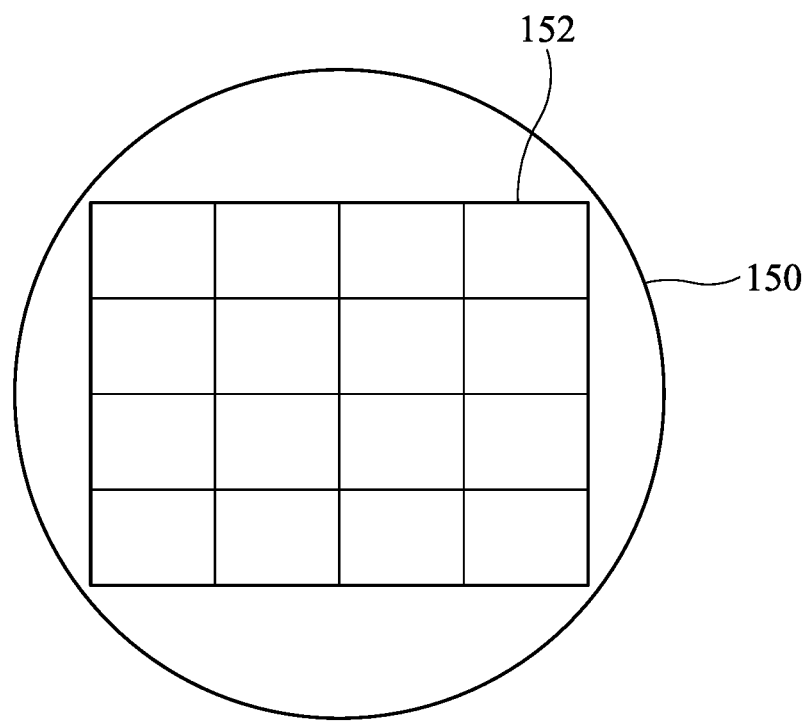
FIG. 7 is a schematic view of a circular silicon chip with a grid etched into the chip that will be diced to form silicon/silica nitride chips according to an embodiment of this invention.

By the term "chip," a semiconductor chip is meant, fabricated using semiconductor methods. The substrate may be cut as a square or rectangle and may also be circular. For example, the chips 1.5 mm to 10.0 mm wide and long may be fabricated from a 2 inch-diameter (5 cm) wafer 150, in which a grid of grooves 152 are cut or etched. This is shown schematically in FIG. 7. The grid 152 is then diced to obtain chips of suitable size for this invention.

By the term "SiN" in the figures or text of this patent application, silicon nitride ($Si_3N_4$) is meant.

In an embodiment, the chip 100 has an upper surface (116) and lower surface (118). The upper and lower surfaces may be referred to alternatively herein as "superior" and "inferior" surfaces.

In an embodiment, a layer of silicon nitride (110) may be provided that forms the top surface (116) of chip 100. Silicon nitride 110 may have a thickness of about 20 nm to about 500 nm. Alternatively, silicon nitride 110 may be about 100 nm to 300 nm thick. Alternatively, silicon nitride 100 may have a thickness of 200 nm. Optionally the chip may have a bottom layer (112) of silicon nitride that forms bottom surface 118. Alternatively, bottom surface 118 may be the bottom of silicon substrate 114. Layer 112, if present, may have a thickness of 20 nm to 500 nm. In an embodiment, layer 112 may be about 100 nm to 300 nm thick. Alternatively, silicon nitride 112 may have a thickness of about 200 nm.

Figure 1B:
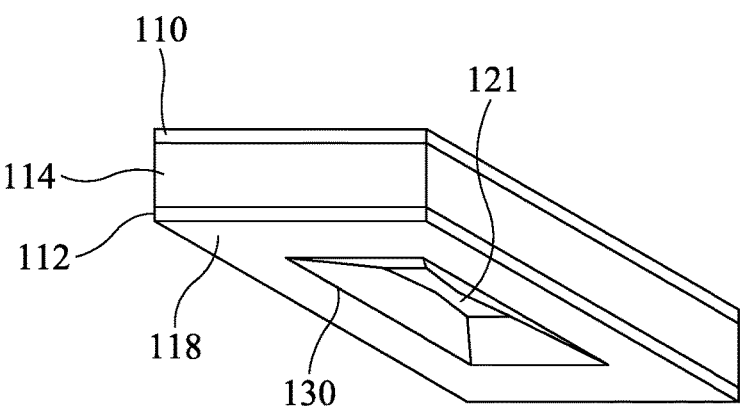
FIG. 1B is a perspective view of the bottom of a silicon/silica nitride chip according to an embodiment.
Figure 3A:
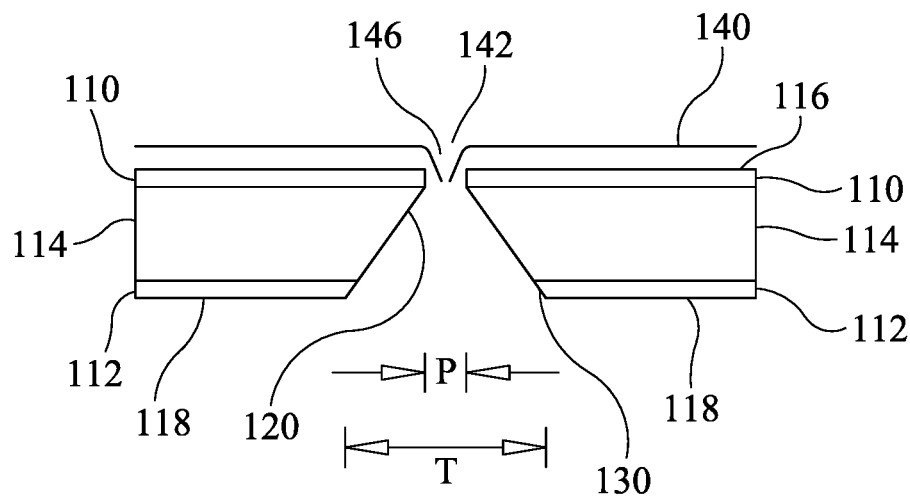
FIG. 3A is a cross section of a silicon/silica nitride chip as shown through the line marked A-A' in FIG. 2. In this embodiment, a window is formed from the bottom of the chip by chemical etching, which creates a frustopyrimidal cavity.

In the center of the bottom of the chip there may be a square window 130 (FIG. 1B). Alternatively, window 130 may be referred to has an "opening." A cross section of window 130 is shown in FIG. 3A. If a bottom layer 114 of silicon nitride is provided, window 130 penetrates the bottom layer. The opening may penetrate from the bottom face of the chip through the silicon substrate to the top silicon nitride layer and does not penetrate the top silicon nitride layer. In an embodiment, the upper boundary of the opening is a square window, about 5 µm to 100 µm (preferably 20 µm) (dimension P) at the top of the substrate. The window 130 may be formed by potassium hydroxide (KOH) etching. KOH etching will produce walls in the silicon substrate having an angle of 54.7°, so the walls will not be vertical [13]. The opening as just described will therefore be a truncated square pyramid, also referred to as frustopyramid, with the truncated top of the pyramid (the "window") forming a square about 5 µm to about 100 µm (preferably 20 µm) (dimension P) on a side. The base of the pyramid has edges with dimension T. For a 20 μm top of the frustopyramid and a 200 μm thick substrate, the base of the square frustopyramid will be about 302 μm on each side because of the angle of KOH etching in silicon. Also illustrated in FIG. 3A is multilayer graphene sheet 140 and optional nanopore 146.

Figure 2:
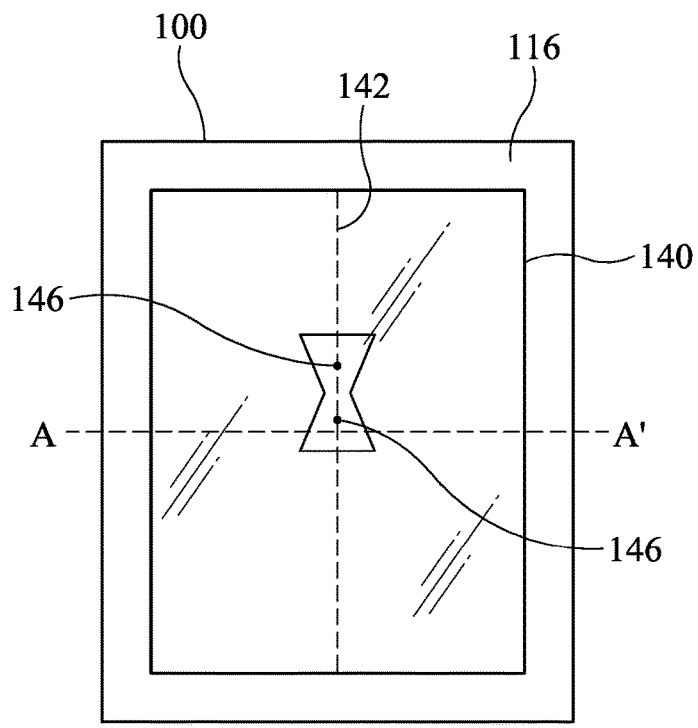
FIG. 2 is a top view of a silicon/silica nitride chip according to an embodiment. A graphene sheet is shown.
Figure 4:
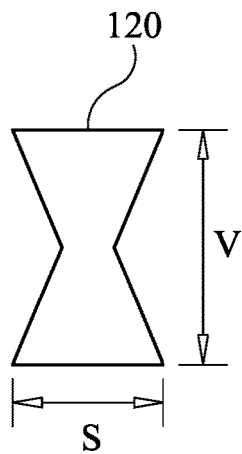
FIG. 4 is a schematic of an hourglass opening in the top of the chip of this invention.

In an embodiment, a hole 120 is provided in the in top layer of silicon nitride centered over the window (FIGS. 2 and 4), wherein the hole is about 50 nm to about 1000 nm wide (preferably 350-400 nm) (FIG. 4, dimension S) and about 50 nm to 1000 nm long (preferably about 500-600 nm) (FIG. 4, dimension U), wherein the hole is in the shape of a circle or simple polygon. In an embodiment, the hole may have an hourglass shape (120) as shown in FIG. 4. In another embodiment, the hole is 350-500 nm wide and 350-500 nm long and comprises a simple polygon selected from a circle, a triangle, a square, a rectangle, and a hexagon.

Figure 3B:
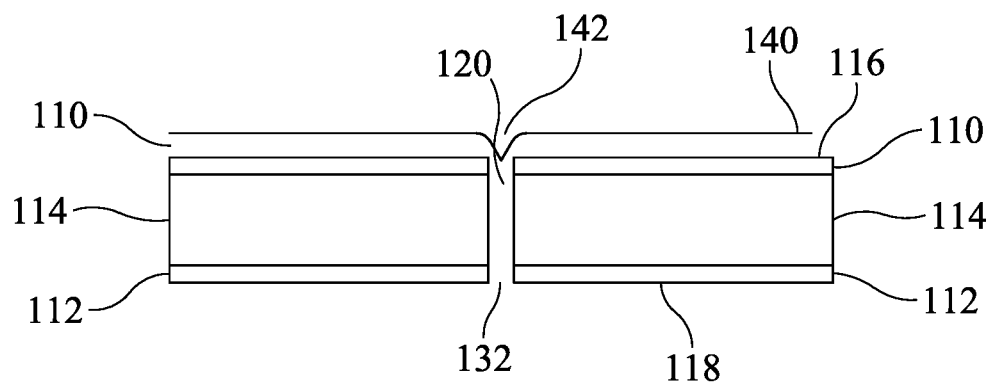
FIG. 3B is a cross section of a silicon/silica nitride chip according to an alternative embodiment wherein the hole is drilled through the chip.
Figure 3C:
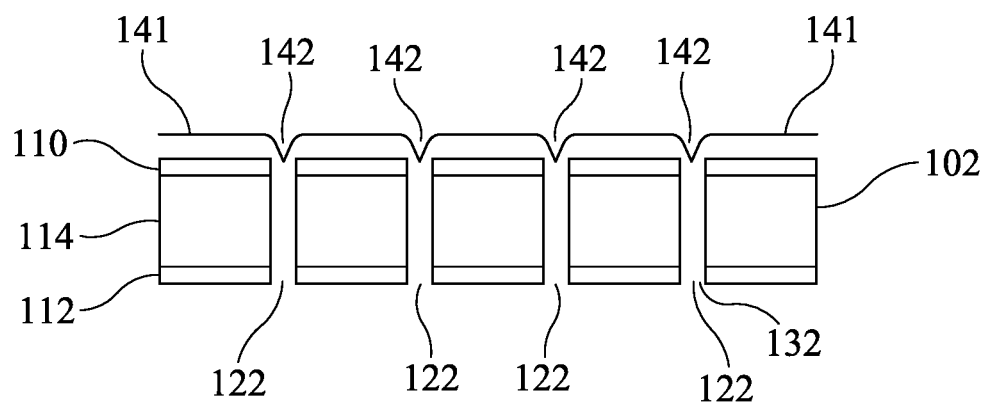
FIG. 3C is a cross section of a silicon/silica nitride chip according to an alternative embodiment wherein a plurality of holes are drilled through the chip. In this embodiment, there may be a grid of holes. Four holes are shown.

Alternatively, holes 120 may be formed by drilling with a microscopic method such as with a transmission electron microscope (TEM) or electron beam technology (FIGS. 3B and 3C). Holes fabricated by drilling will not have a window with angled walls as in 130. Rather, a straight shaft 132 will perforate the entire thickness of the chip. Also shown is graphene sheet 140 or 141, without nanopores.

Figure 6A:
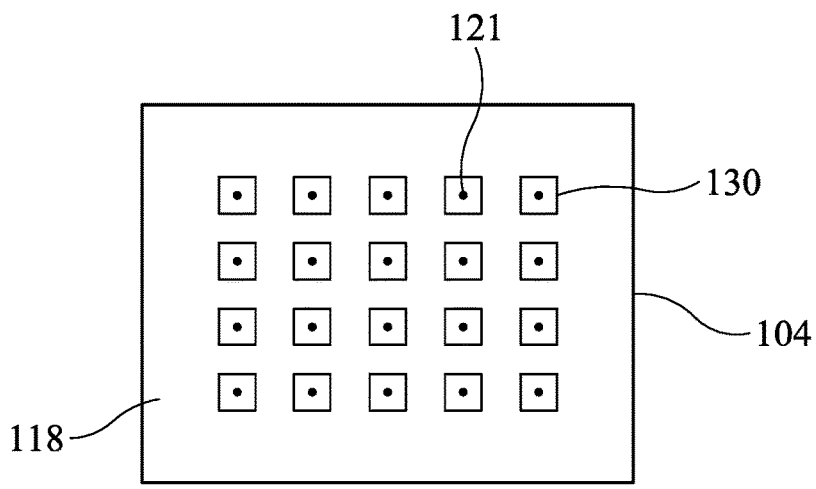
FIG. 6A is an elevation view of the bottom of a chip according to an embodiment of this invention with a grid showing a plurality of windows formed by chemical etching, with a hole in each window.
Figure 6B:
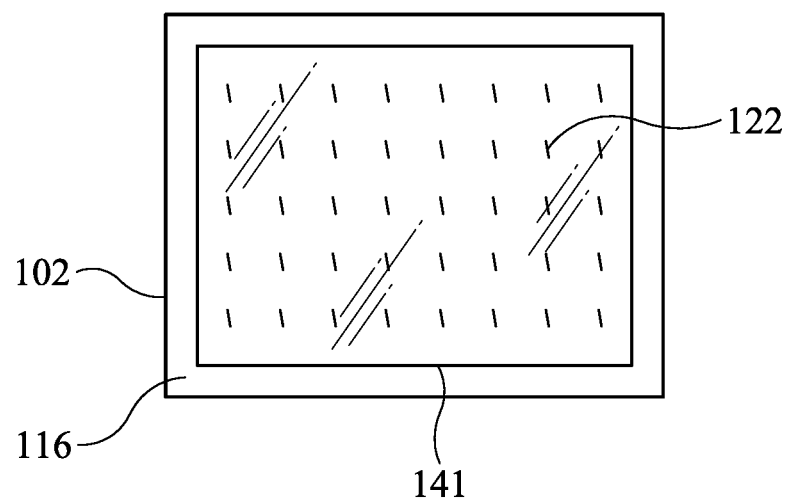
FIG. 6B is an elevation view of the top of a chip according to this invention with a larger grid of holes (122) formed by drilling.

In a further embodiment, a plurality of holes 122 may be provided, in which, for example, a grid or array of holes and windows is formed on the chip 100. This is shown in FIGS. 6A and 6B. FIG. 6A shows the bottom 118 of a chip 104 having a grid of etched windows 130. Also shown are holes 121 in each window 130. Holes 121 are the bottom of holes 120. With etched windows 130, the grid can be up to about 10×10, and may be smaller, for example 6×6, 5×5, or 4×4.

Another embodiment of a plurality of holes is shown in FIG. 6B, which is a top elevation view of a chip 102 with a plurality of holes 122. In an embodiment as illustrated, the drilled holes are straight shafts 132. The grid or array in this embodiment can have more holes than with the etched method, up to a 100×100 grid. The grid can also be smaller, for example, a 30×30 grid, a 20×20 grid, or a 10×10 grid. FIG. 6B shows an MLG sheet 141 laid over the grid. In an embodiment, the sheet is affixed to surface 116 after the holes 122 are drilled, and then nanopores 146 are drilled (not shown). This embodiment with drilled holes is also illustrated in FIG. 3C, showing a cross section of a chip 102 with a plurality of drilled holes 122.

In the array embodiments of FIGS. 6A and 6B, arrays of electrodes may be used to measure electrical potential across each hole in the grid. [14, 15]

Figure 5:
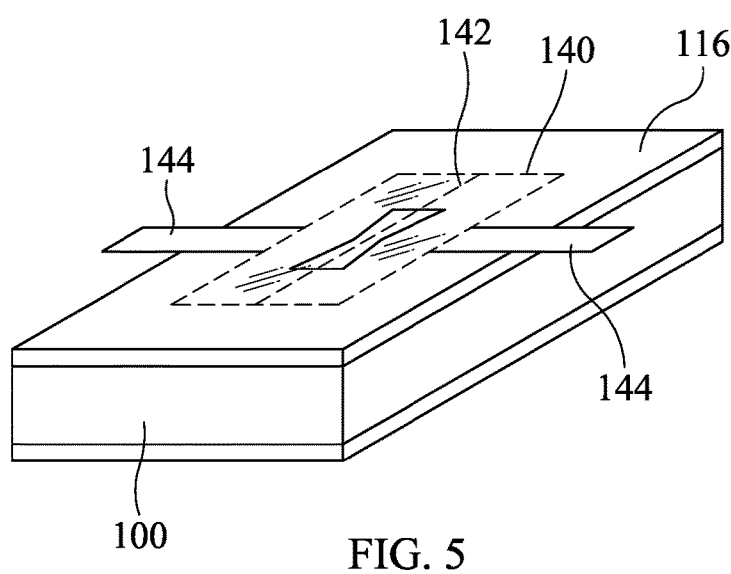
FIG. 5 is a perspective view of the top of a chip according to this invention having a graphene sheet across the top, a fold in the graphene over the opening, nanopores in the fold, and two electrodes.

In an embodiment, the graphene sheet 140 about 1-60 nm thick is placed over the top surface of silicon chip (FIGS. 2, 3, and 5) in a latitudinal orientation, and wherein the graphene sheet is subjected to lateral compression to cause a p-type crinkle ruga having a crease to form thereon over each hole 120 in the biosensing chip. The graphene may be a sheet of multilayer graphene (MLG), that may be 2-7 sheets (or more) of graphene, placed over the chip surface. The graphene will naturally adhere to the silicon nitride surface. Lateral pressure may be applied to cause a p-type crinkle ruga having a crease or fold to form over the hole. Optionally, one or more nanopores 146 (FIG. 2) in the graphene sheet, wherein the nanopores are about 0.3 to about 10 nm in diameter, may be provided over the hole. Transmission electron microscopy (TEM) or electron beam technology may be used to drill the required nanopores in the graphene creases.

In an embodiment, the nanopores 146 drilled in the MLG have microfluidic capabilities to capture and transport DNA with beads. "Microfluidics" refers to the behavior, precise control, and manipulation of fluids that are geometrically constrained to a small scale (typically sub-millimeter) at which surface forces dominate volumetric forces. The benefit of this design is that droplets can transport DNA, efficiently speeding up the single cell sequencing process, and be pulled into the graphene crinkle crease within the Si by attracting DNA easily with the positive charge located in the crease. The crinkle also physically draws the droplet into the crease, making nanopore transition and making translocation much easier, combined with the positive charge in the graphene layers. Current nanopore technologies using conventional flat substrates (for example, [16]) cannot incorporate droplets due to having to aim a large droplet perfectly over a sub 2-nm pore and reliably lead DNA to the nanopore once in solution. The inventive design allows droplets to be captured in a structure first, then positive charges pull and align DNA into the nanopore, allowing easier translocation into the nanopore that is 2 nm wide or less. Integrated microfluidic systems can flush the nanopore with electrolyte solution to allow electrophoretic translocation.

In an embodiment, gel beads may be used to transport DNA molecules to the inventive sequencing chips. Gel beads, containing barcoded oligonucleotides, are mixed with a sample, which can be high molecular weight (HMW) DNA. Gel Beads and samples are then added to an oil-surfactant solution to create "Gel Beads in Emulsion" (GEMs), which act as individual reaction vesicles in which the Gel Beads are dissolved and the sample is barcoded (see [17]). In some cases, barcoded products are pooled for downstream reactions to create short-read sequencer compatible libraries. In an embodiment of this invention, these fragments would be sequenced directly, to read differences in bases between cells for similar fragments of DNA in similar regions of interest in their genomes, and also to directly map back to the original cells by reading the barcode sequence directly, due to label-free nanopore sequencing that can capture these droplets (where then separation would occur between the bead and DNA) and sequence single-cell transcriptomes in a highly parallel manner. After sequencing, the resulting barcoded short read sequences may be analyzed with bioinformatics that use the barcode information to map reads back to their original DNA sequences.

Figure 8:
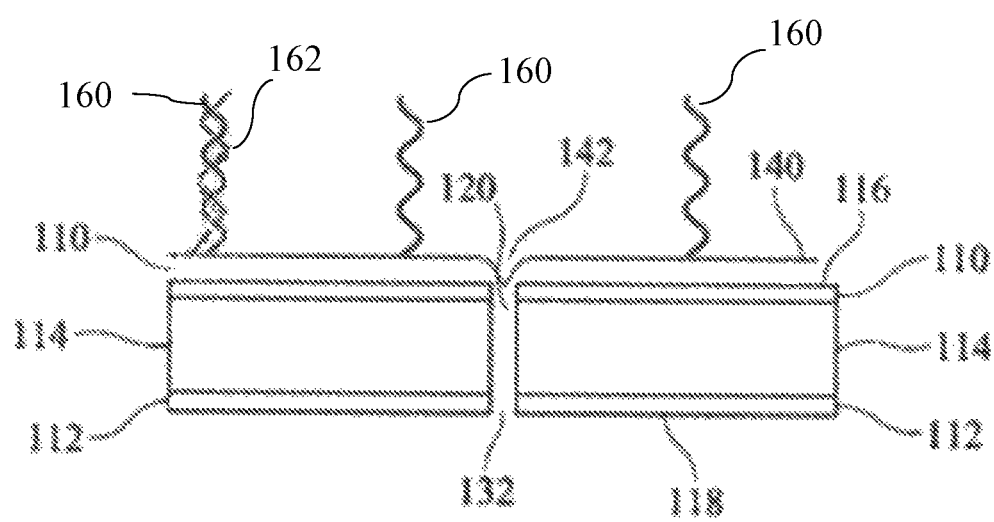
FIG. 8 is a schematic of an embodiment of this invention with DNA probes linked to the graphene sheet 140.

In an embodiment, one or more nucleic acid probes 160 may be covalently bound to MLG 140 (FIG. 8) [3]. The probes can hybridize to complementary nucleic acid strands 162 during sensing or sequencing operations of the inventive biosensing chips. FIG. 8 shows three nucleic acid probes 160, wherein one on the probes is hybridized to a complementary strand 162. In a DNA/RNA sensing embodiment, the probes hybridize with a complementary nucleic acid sequence, which causes characteristic changes in the electrical potential across the hole 120 that can be detected to confirm that the appropriate DNA/RNA sequence is present in a sample passed across the sensor. In a nucleic acid sequencing embodiment, the probes 160 may tend to increase the interactions of the MLG with the nucleic acid sample which may improve the sensitivity of the sequencing process. In an embodiment, the probes 160 are bonded to the MLG as close to or within the crinkle 142 as possible, which is closest to the electrical hotspot for increased sensitivity of hybridization events.

In an embodiment, a pair of electrodes 144 (FIG. 5) on the graphene sheet on opposite ends of each hole 120 are provided, where the electrodes are connected to a patch clamp amplifier capable of measuring an electric charge across the graphene sheet.

In an embodiment, a method is provided of detecting nucleobases in a strand of nucleic acids, comprising a chip with a graphene sheet connected to a patch clamp amplifier, and directing a saline solution of the nucleic acid comprising a strand of nucleobases toward a nanopore in the graphene sheet, wherein the nucleobase strand translocates through the pore and interacts with the layers of the multilayer graphene sheet, and the patch clamp amplifier measures changes in the ionic current and detects each nucleobase in the nucleic acid strand translocating through the nanopore and the nucleic acid sequence is assigned.

In an embodiment, the instant invention may improve measurements by using the positive charge within the graphene crinkle 142 as a way to electronically probe and electrostatically position each nucleotide within the pore. Nucleotide strands directed towards a pore on the graphene will separate and translocate through the pore and the hole on the chip. The positive charge attraction to the negatively charged DNA molecule will also slow down the translocation, providing a means to control translocation while potentially simplifying measurement of ionic current in 0.3-1M KCl solution to single base resolution using charges within the graphene to 1) position nucleotides within the pore with more reliable orientation within the pore, while also 2) forming temporary electrostatic interactions with nucleotides for enhanced single base resolution, and 3) analyzing charge characteristics of specific nucleobases.

Measurements of ionic current can be efficiently conducted under 120-180 mV potentials across the membrane with electrical detection equipment such as a patch clamp amplifier, for example, an Axon™ Axopatch™ 200B. The electric signatures as ionic current fluctuations occur during DNA translocation through the nanopore and caused by blockages within the nanopore will be converted to nucleobase-specific reads by circuitry that records information from the amplifier or patch equipment, thereby assigning specific nucleobases that are passing through the nanopore or hole in the biosensing chip. Fluctuations of the ionic current will reflect the charge in the graphene crinkle at the single-base level in a millisecond time scale directly correlating to nanoscale electronic interactions between the polarization within the graphene layers and the nucleotides. Information will be obtained and converted into nucleobase assignments as a readable format via specialized software that utilizes algorithms for translation of known electronic signatures within ionic current measurements taken during sequencing runs. The potential for less noise and increased signal quality is evident, as the positive charge within the graphene crinkle will slow down translocation and potentially improve signal quality, thereby removing the need for increased electrolyte solution to slow down DNA translocation in conventional nanopore methods [19]. Compatibility for droplet delivery methods are also implied, since the natural curvature of the crinkle as well as charge polarization will work together to draw DNA into the nanopore without need for delicate enzymes or complex microfluidic processes. Such a benefit would add multiplexed, real-time single cell sequencing technologies to the field that also preserve sample quality and directly analyze physical, structural, and epigenomic properties of DNA via electronic probing, which contribute a new layer of data to single cell analyses per run with drastically reduced chemical preparation in shorter timeframe.

REFERENCE NUMBER LISTING

No. Description
- 100 Semiconductor biosensing chip
- 102 Semiconductor biosensing chip with plurality of drilled windows
- 104 Semiconductor biosensing chip with plurality of etched windows
- 105 Circular silicon chip
- 106 Circular silicon chip with grid
- 110 Superior (top) silicon nitride ($Si_3N_4$) layer
- 112 Inferior (bottom) silicon nitride ($Si_3N_4$) layer
- 114 Silicon substrate layer
- 116 Superior (top) surface of biosensing chip 100
- 118 Inferior (bottom) surface of biosensing chip 100
- 120 hole
- 121 Hole (bottom view)
- 122 Plurality of drilled holes
- 130 Window—formed by etching with angled walls
- 132 Shaft through chip formed by drilling
- 140 Multilayer graphene (MLG) sheet
- 141 MLG layered over a plurality of holes
- 142 Fold or crinkle in MLG
- 144 Electrode
- 146 Nanopore in MLG
- 150 5 cm diam chip with grid of biosensing chips etched thereon
- 152 Grid of biosensing chips etched onto 5 cm diameter chip
- 160 Nucleic acid strand probe
- 162 Complementary nucleic acid polymer hybridized with nucleic acid probe

BIBLIOGRAPHY

1. Traversi, F.; Raillon, C.; Benameur, S. M.; Liu, K.; Khlybov, S.; Tosun, M.; Krasnozhon, D.; Kis, A.; Radenovic, A., Detecting the translocation of DNA through a nanopore using graphene nanoribbons. *Nature Nanotechnology* 2013, 8, 939-945, DOI: 10.1038/nnano.2013.240.
2. Heerema, S. J.; Dekker, C., Graphene nanodevices for DNA sequencing. *Nature Nanotechnology* 2016, 11, 127-136, DOI: 10.1038/nnano.2015.307.
3. Hwang, M. T.; Heiranian, M.; Kim, Y.; You, S.; Leem, J.; Taqieddin, A.; Faramarzi, V.; Jing, Y.; Park, I.; van der Zande, A. M.; Nam, S.; Aluru, N. R.; Bashir, R., Ultrasensitive detection of nucleic acids using deformed graphene channel field effect biosensors. *Nature Communications* 2020, 11, 1543, DOI: 10.1038/s41467-020-15330-9.
4. Verschueren, D. V.; Pud, S.; Shi, X.; De Angelis, L.; Kuipers, L.; Dekker, C., Label-Free Optical Detection of DNA Translocations through Plasmonic Nanopores. *ACS Nano* 2019, 13, 61-70, DOI: 10.1021/acsnano.8b06758.
5. Feng, Y.; Zhang, Y.; Ying, C.; Wang, D.; Du, C., Nanopore-based Fourth-generation DNA Sequencing Technology. Genomics, *Proteomics & Bioinformatics* 2015, 13, 4-16, DOI: https://doi.org/10.1016/j.qpb.2015,01,009.
6. Optical system and assay chip for probing, detecting and analyzing molecules. U.S. Pat. No. 9,921,157, Mar. 20, 2018.
7. Li, R.; Kothari, M.; Landauer, A. K.; Cha, M.-H.; Kwon, H.; Kim, K.-S., A New Subcritical Nanostructure of Graphene—Crinkle-Ruga Structure and Its Novel Properties. *MRS Advances* 2018, 3, 2763-2769, DOI: 10.1557/adv.2018.432.

8. Paulechka, E.; Wassenaar, T. A.; Kroenlein, K.; Kazakov, A.; Smolyanitsky, A., Nucleobase-functionalized graphene nanoribbons for accurate high-speed DNA sequencing. *Nanoscale* 2016, 8, 1861-1867, DOI: 10.1039/C5NR07061A.
9. Derrington, I. M.; Butler, T. Z.; Collins, M. D.; Manrao, E.; Pavlenok, M.; Niederweis, M.; Gundlach, J. H., Nanopore DNA sequencing with MspA. *Proceedings of the National Academy of Sciences* 2010, 107, 16060-16065, DOI: 10.1073/pnas.1001831107.
10. Manrao, E. A.; Derrington, I. M.; Pavlenok, M.; Niederweis, M.; Gundlach, J. H., Nucleotide Discrimination with DNA Immobilized in the MspA Nanopore. *PLOS ONE* 2011, 6, e25723, DOI: 10.1371/journal.pone.0025723.
11. Venkatesan, B. M.; Dorvel, B.; Yemenicioglu, S.; Watkins, N.; Petrov, I.; Bashir, R., Highly Sensitive, Mechanically Stable Nanopore Sensors for DNA Analysis. *Advanced Materials* 2009, 21, 2771-2776, DOI: https://doi.org/10.1002/adma.200803786.
12. Liu, S.; Zhao, Q.; Xu, J.; Yan, K.; Peng, H.; Yang, F.; You, L.; Yu, D., Fast and controllable fabrication of suspended graphene nanopore devices. *Nanotechnology* 2012, 23, 085301, DOI: 10.1088/0957-4484/23/8/085301.
13. Centre, U.o.A.n.F.C., KOH Etching of Bulk Silicon. Alberta, U.o., Ed.2013.
14. Stranges, P. B.; Palla, M.; Kalachikov, S.; Nivala, J.; Dorwart, M.; Trans, A.; Kumar, S.; Porel, M.; Chien, M.; Tao, C.; Morozova, I.; Li, Z.; Shi, S.; Aberra, A.; Arnold, C.; Yang, A.; Aguirre, A.; Harada, E. T.; Korenblum, D.; Pollard, J.; Bhat, A.; Gremyachinskiy, D.; Bibillo, A.; Chen, R.; Davis, R.; Russo, J. J.; Fuller, C. W.; Roever, S.; Ju, J.; Church, G. M., Design and characterization of a nanopore-coupled polymerase for single-molecule DNA sequencing by synthesis on an electrode array. *Proceedings of the National Academy of Sciences* 2016, 113, E6749-E6756, DOI: 10.1073/pnas.1608271113.
15. INTEGRATED SENSOR ARRAYS FOR BIOLOGICAL AND CHEMICAL ANALYSIS. U.S. Pat. No. 8,936,763 B2, Jan. 20, 2015.
16. Rang, F. J.; Kloosterman, W. P.; de Ridder, J., From squiggle to basepair: computational approaches for improving nanopore sequencing read accuracy. *Genome Biology* 2018, 19, 90, DOI: 10.1186/s13059-018-1462-9.
17. NXTGNT 2020 https://www.nxtgnt.ugent.be/10x-genomics-single-cell-and-linked-read-sequencing/ (Accessed: Nov. 4, 2020).
18. Deamer, D. W.; Branton, D., Characterization of Nucleic Acids by Nanopore Analysis. *Accounts of Chemical Research* 2002, 35, 817-825, DOI: 10.1021/ar000138m.
19. Wang, Y.; Yang, Q.; Wang, Z., The evolution of nanopore sequencing. *Frontiers in Genetics* 2015, 5, DOI: 10.3389/fgene.2014.00449.

The invention claimed is:

1. A sequencing chip for sequencing a strand of nucleic acids comprising
   a. a chip formed from a substrate fabricated from silicon about 1.0 mm to about 10 mm wide, about 1.0 mm to about 10 mm long, with a thickness of about 50 μm to 500 μm;
   b. wherein the substrate has a top layer of silicon nitride ($Si_3N_4$) with a thickness of 20 nm to 500 nm;
   c. wherein the substrate optionally has a bottom layer of silicon nitride with a thickness of 20 nm to 500 nm;
   d. wherein the formed chip has at least one hole drilled by a microscopic method in the top layer of silicon nitride and that penetrates the entire thickness of the chip, and wherein the hole is 50 nm to 1000 nm wide and 50 nm to 1000 nm long, wherein the hole is in the shape of a circle or simple polygon;
   e. wherein a multilayer graphene sheet about 1-60 nm thick is affixed to the $Si_3N_4$ layer on the top substrate in a latitudinal orientation, and wherein the graphene sheet is subjected to lateral compression to cause a p-type crinkle ruga having a crease to form thereon over the at least one hole; and
   f. wherein a pair of electrodes is provided on opposite ends of each hole on the graphene sheet, where the electrodes are connected to electrical detection equipment capable of measuring an ionic current across the graphene sheet and wherein fluctuations in the ionic current of a nucleic acid strand as it interacts with the graphene sheet are measured by the electrical detection equipment and converted into nucleobase assignments.

2. The sequencing chip of claim 1, wherein the graphene sheet comprises one or more nanopores about 0.3 to about 10 nm in diameter centered over the hole, such that a nucleic acid polymer strand can translocate through at least one nanopore and wherein fluctuations in the ionic current of a nucleic acid strand translocating through at least one nanopore are measured by the electrical detection equipment and converted into nucleobase assignments.

3. A method of detecting nucleobases in a strand of nucleic acids, comprising a sequencing chip with a graphene sheet containing at least one or more nanopores according to claim 2 and directing a saline solution of the nucleic acid comprising a strand of nucleobases toward a nanopore in the graphene sheet, wherein the nucleobase strand translocates through the pore and interacts with the layers of the multilayer graphene sheet, and wherein a patch clamp amplifier connected to the electrodes at each hole measures changes in the ionic current and detects each nucleobase in the nucleic acid strand translocating through the nanopore and the nucleic acid sequence is assigned.

4. The sequencing chip of claim 1, wherein the graphene sheet has no nanopores and wherein the fluctuations in the ionic current across the at least one hole caused by a nucleic acid polymer interacting with the crinkle ruga on the graphene sheet are measured by the electrical detection equipment and converted into nucleobase assignments.

5. A method of sensing nucleobases in a strand of nucleic acids, comprising a sequencing chip with a graphene sheet according to claim 4 and directing a saline solution of the nucleic acid comprising a strand of nucleobases toward the crinkle ruga on the graphene sheet, wherein the nucleobase strand interacts with the multilayer graphene sheet, and wherein a patch clamp amplifier connected to the electrodes at each hole measures changes in the ionic current and electrical characteristics of the nucleic acid strand to detect each nucleobase in the nucleic acid strand and the nucleic acid sequence is assigned.

6. The sequencing chip of claim 1, wherein the substrate is about 1.5 mm to about 3.0 mm wide and about 1.5 mm to about 3.0 mm long.

7. The sequencing chip of claim 1, wherein the substrate has a top layer of silicon nitride ($Si_3N_4$) with a thickness of about 200 nm.

8. The sequencing chip of claim 1 wherein the substrate has a bottom layer of silicon nitride with a thickness of 100 nm to 300 nm or the substrate has a bottom layer of silicon nitride with a thickness of about 200 nm.

9. The sequencing chip of claim 1 wherein the substrate has a bottom layer of silicon nitride with a thickness of about 200 nm.

10. The sequencing chip of claim 1, wherein the at least one hole is selected from at least one of the group consisting of a circle, a triangle, a square, a rectangle, a hexagon and an hourglass shape.

11. The sequencing chip of claim 1, further comprising a grid of holes in the chip, wherein the grid is up to a up to a 100×100 grid, or up to a 20×20 grid, or up to a 10×10 grid.

12. The sequencing chip of claim 11, further comprising an array of electrodes.

13. The sequencing chip of claim 1, further comprising one or more nucleic acid probes bound to the multilayer graphene sheet.

14. The sequencing chip of claim 1 further comprising at least one opening defining the base of a square frustopyramid penetrating from a bottom surface of the substrate into a top surface of the substrate of the chip, wherein the opening does not penetrate the top layer of silicon nitride, and wherein the top of the square frustopyramid is a square window about 5 μm to about 100 μm on each side.

15. The sequencing chip of claim 1 wherein the at least one hole in the top layer of silicon nitride centered over the window is about 350 nm to about 500 nm wide and about 350 nm to about 1000 nm long.

* * * * *